United States Patent [19]

Hartlaub

[11] Patent Number: 4,552,154
[45] Date of Patent: Nov. 12, 1985

[54] WAVEFORM MORPHOLOGY DISCRIMINATOR AND METHOD

[75] Inventor: Jerome T. Hartlaub, New Brighton, Minn.

[73] Assignee: Medtronic, Inc., Minneapolis, Minn.

[21] Appl. No.: 588,277

[22] Filed: Mar. 12, 1984

[51] Int. Cl.[4] .................................................. A61B 5/04
[52] U.S. Cl. .............................. 128/702; 128/419 PG
[58] Field of Search .................. 128/419 PG, 702–705

[56] References Cited

U.S. PATENT DOCUMENTS

| | | | |
|---|---|---|---|
| 3,144,019 | 8/1964 | Haber | 128/705 |
| 3,524,442 | 8/1970 | Horth | 128/703 |
| 3,658,055 | 4/1972 | Abe et al. | 128/703 |
| 3,829,766 | 8/1974 | Herz | 128/704 |
| 4,388,927 | 6/1983 | Schober | 128/419 PG |

*Primary Examiner*—William E. Kamm

*Attorney, Agent, or Firm*—Robert C. Beck; John L. Rooney; Joseph F. Breimayer

[57] ABSTRACT

A waveform detection system for use in a pacemaker for distinguishing normal beats from ectopic or abnormal beats for example, such as those involving ventricular tachycardia, ventricular flutter or fribrillation, premature ventricular beats, supraventricular tachycardia, retrograde conduction; and in dual chamber or atrial applications those involving atrial tachycardia and atrial flutter or fibrillation. The term "abnormal" is employed herein to mean all abnormal beats including those specified above. In the system of the illustrated embodiment a sense amplifier is employed for initiating a counter in response to a detected cardiac event and a voltage controlled oscillator is used for converting the instantaneous value of the applied waveform to a bit rate delivered to the counter. The morphology or shape of the physiological waveform is represented by a number present in the counter at the end of the counting cycle which allows for a therapy decision to be made.

4 Claims, 4 Drawing Figures

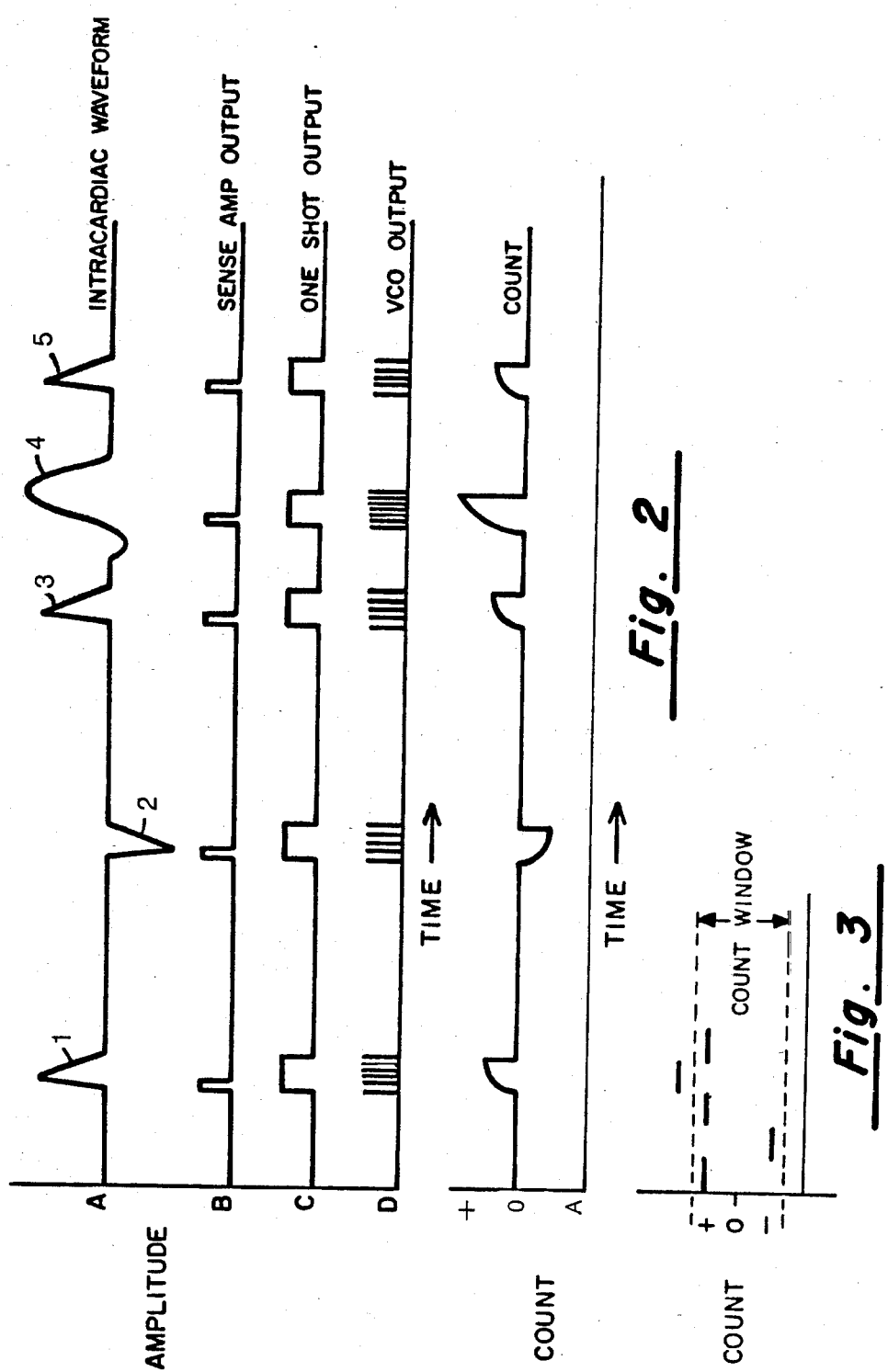

WAVEFORM MORPHOLOGY DISCRIMINATOR AND METHOD

BACKGROUND OF THE INVENTION

1. Field of the Invention

This invention relates to implanted medical devices and, more particularly relates to a physiological waveform morphology discriminator and method for use in a pacemaker for characterizing the origin of cardiac depolarizations.

2. Description of the Prior Art

A variety of disease mechanisms may result in cardiac dysrhythmias. Typically these dysrhythmias are characterized by electrical instability in the cardiac tissue which results in abnormal mechanical activity of the heart. The abnormal mechanical activity results in the reduction of the rate at which oxygenated blood is circulated throughout the body. The parameter is called cardiac output. If the loss of cardiac output results from a heartbeat slower than a normal heartbeat responding to the same physiologic demand, the dysrhythmia is called a bradycardia. In contrast, an abnormally rapid beating of the heart which also results in reduced cardiac output is generically termed a pathologic tachycardia.

Pacers for the treatment of bradycardia are known from U.S. Pat. No. 3,478,746 to Greatbatch. This patent teaches a demand type (VVI) pacemaker which provides a stimulus to cardiac tissue through a pacing lead; if no naturally occurring cardiac activity is sensed within a preset time period referred to as the escape interval. Consequently, the stimulating pulses are supplied to the heart only when the intrinsic heart rate drops below a preset minimum corresponding to this escape interval.

The intrinsic heart rate is detected by a demand pacer through a sense amplifier. A sense amplifier typically provides passband amplification at the frequencies which predominate in the intracardiac signal as obtained from the left ventricle. The amplification stage is typically followed by a level detection stage which provides a logic level output if the input physiological waveform meets both passband and amplitude criteria. Examples of sense amplifiers as used in demand pacers include the device taught by U.S. Pat. No. 3,927,677 to Gobeli.

More recent pacers have been proposed for the treatment of tachycardia. Both U.S. Pat. Nos. 3,698,398 and 3,693,627 to Berkovits teach the use of a pacer therapy to treat a tachyarrhythmia. Like a demand pacer, the tachy treatment pacer utilizes a sense amplifier to detect the cardiac depolarizations. Typically the tachyarrhythmia treatment therapy is invoked when the rate of cardiac depolarizations as measured by the sense amplifier reach a preset limit between 120 beats per minute and 200 beats per minute. There are two problems associated with the use of a simple rate detection system for the detection of a pathologic tachyarrhythmia. One problem is that pathologic tachyarrhythmias can have rates within the range shared by normal heart activity. There is, in effect, an overlap between the physiologically normal heart rate which does not require treatment and the pathologic heart rate which does require therapy.

An additional problem relates to the detection by the pacer system of beats of ectopic or abnormal origin. A normal heat beating at a physiologically normal rate may be interrupted by occasional premature ventricular contractions (PVC). These PVC's appear on the EKG interspersed among sinus beats in the patient's electrocardiogram. Consequently, a rate detection algorithm operating on sensed depolarizations detected by a sense amplifier could interpret a PVC as a tachyarrhythmia.

The PVC as well as other beats of abnormal origin differ in their shape or morphology from a normally conducted sinus beat. Typically, for example, the amplitudes and durations associated with PVC's are larger than those associated with normal beats and the slope or rise time of the signal is somewhat less than the intrinsic deflection of a normally conducted R-wave. These time domain differences in the signal do not produce substantial changes in the frequency spectra of the signal. As a consequence, conventional sense amplifiers relying on frequency domain parameters such as bandpass amplification are incapable of distinguishing normally conducted R-waves from abnormal beats despite the differences in their time domain morphology.

The ability to distinguish between ectopic beats and sinus beats would aid immeasurably in the formulation of pacer therapies for cardiac dysrhythmias in general, and tachyarrhythmias in particular.

DESCRIPTION OF THE DRAWINGS

FIG. 2 is a collection of waveforms depicting the operation of the system.

FIG. 3 is a flow chart describing the operation of the invention.

DESCRIPTION OF THE PREFERRED EMBODIMENT

The waveform morphology detector of the present invention includes apparatus and method for producing a numerical index dependent upon the time domain characteristics of the waveform associated with the cardiac depolarization. The value of the numerical index is compared with a reference value to determine whether the candidate waveform has a waveform shape similar to the reference value to assist in providing the correct therapy.

The reference value may be entered into the device through a non-invasive programming system or may be developed by the implanted device based upon a historical average of waveforms associated with normally conducted cardiac depolarizations.

The structure for carrying out the invention includes a counter which is enabled by the output of a one shot. The one shot is initiated by the output of a conventional sense amplifier which detects cardiac activity. After a sensed cardiac depolarization, the counter begins to accumulate counts generated by a voltage controlled oscillator (VCO). The VCO in turn is controlled by the output voltage of a preamplifier. The preamplifier generates an output voltage corresponding to the instantaneous value of the cardiac depolarization. As a consequence, the number in the counter at the end of a preset timing interval reflects the shape of the cardiac depolarization. The timing means for generating the preselected timing interval may be remotely programmed or may be fixed.

Figure 1:
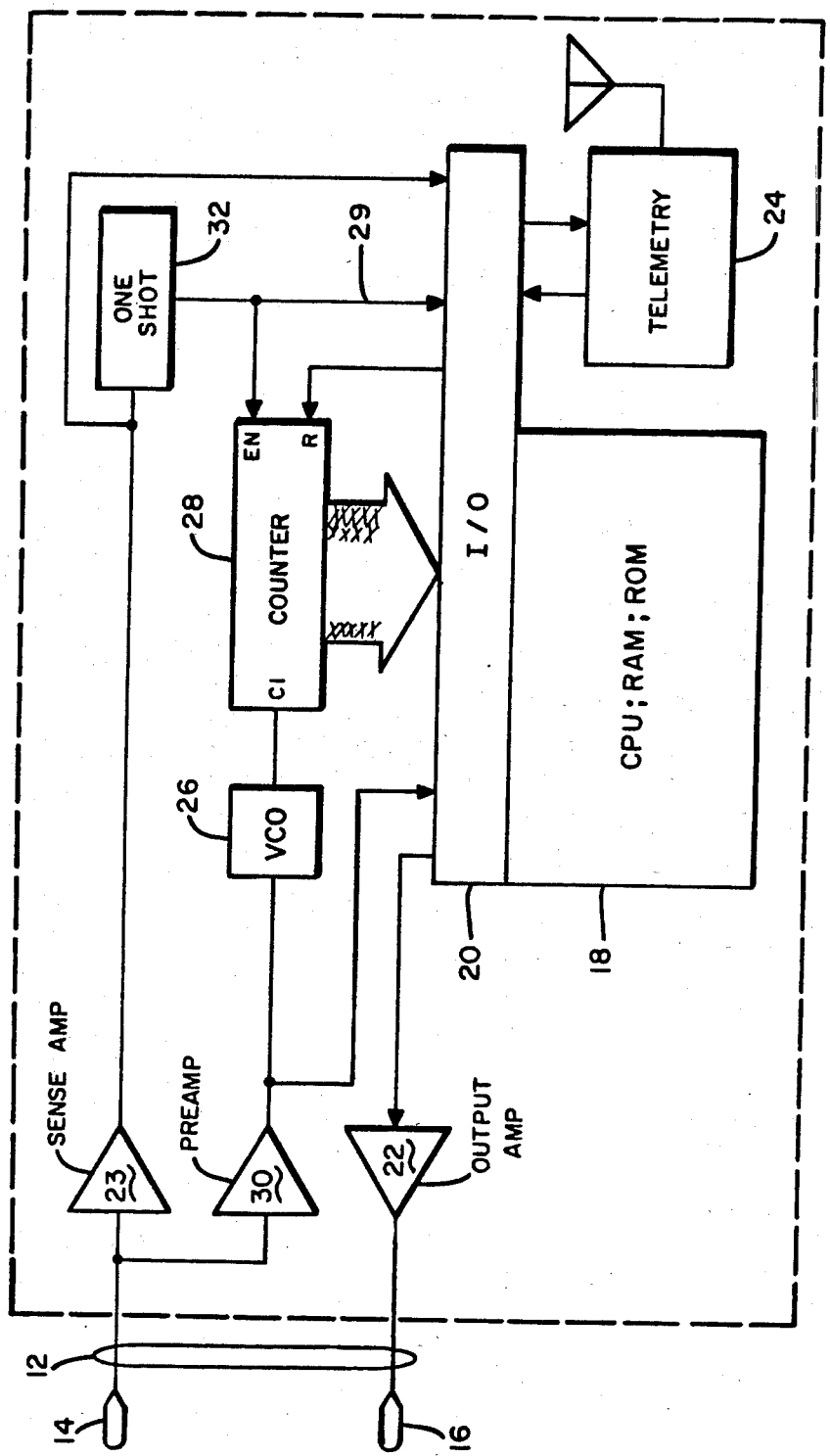
FIG. 1 is a functional block diagram of an implantable pacer incorporating the present invention.

Turning to FIG. 1 there is shown a functional block diagram of a pacer incorporating the present invention. The pacemaker designated generally as 10 is connected to the cardiac tissue through a lead system 12 having a sensing electrode 14 and a stimulating electrode 16.

The pacing function is achieved through software control of a microprocessor system generally designated 18. This system includes a central processing unit (CPU) and volatile (RAM) as well as non-volatile (ROM) memory. The software driven microprocessor system 18 communicates to additional pacer logic through an I/O port 20 which interfaces the pacer with an output amplifier 22 which provides the therapeutic stimulation to the cardiac tissue.

A telemetry system 24 is provided which permits the non-invasive programming of pacing parameters as well as telemetry of information acquired by the implanted device. This pacing system also includes a sense amplifier 23 for detecting the depolarization of cardiac tissue and communicating this information to the CPU. The pacing system may be configured to operate in any of the known pacing modalities including ventricular demand pacing mode (VVI), atrio-ventricular sequential pacing mode (DVI), atrial-synchronized, ventricularly inhibited pacing mode (VDD), dual demand pacing mode (DDD), and tachyarrhythmia pacing modes.

The waveform discriminator apparatus is most useful when the pacemaker operates in a tachyarrhythmia detection and treatment mode. In a tachyarrhythmia treatment mode it is useful to distinguish the origin of sensed cardiac depolarizations since the efficacy of a stimulation or treatment regime depends strongly upon the source and mechanism of a tachyarrhythmia. Conventional rate discrimination arrhythmia detection systems are incapable of accurately characterizing the origin of the arrhythmia and may, in some instances, invoke a therapeutic treatment regime when such treatment is inappropriate. When used in conjunction with the tachyarrhythmia pacer it is anticipated that the waveform morphology discriminator will be one detection criteria which will be satisfied prior to the initiation of a tachyarrhythmia treatment.

Prior art tachyarrthmia treatment devices including that taught by U.S. Pat. No. 3,693,627 to Berkovits operates under VVI mode generating an output stimulus at the end of an external control and delivers a burst of closely paced stimuli through an output amplifier to the cardiac tissue in an effort to disrupt or break up the tachyarrhythmia.

The pacemaker as shown in FIG. 1 may operate in a conventional demand (VVI) mode wherein the sense amplifier 23 will reset a software implemented escape interval timer within the CPU through the I/O port 20. If the sense amplifier does not detect a cardiac depolarization within the preset escape interval an output stimulus will be issued from the output amplifier 22 by a control signal provided to the output amplifier through the I/O port 20.

If the rate of cardiac depolarizations exceeds a preset limit, then a tachyarrhythmia treatment will not be invoked unless the origin and/or nature of the cardiac depolarization is an abnormal one. Traditional sense amplifiers have been unable to determine the origin and nature of cardiac depolarizations since they operate only on the frequency domain characteristics of the intercardiac signal.

By contrast, the physiological waveform discriminator of the present invention relies upon the time domain characteristics or morphology of the input waveform to ascertain its origin and/or nature. In operation, after a cardiac depolarization is initially sensed the sense amplifier 24 will issue an interrupt signal to the microprocessor based pacing system 18 which will enable the voltage controlled oscillator 26 and counter 28. The sense amplifier will also initiate the operation of one-shot 32. The intercardiac waveform present at electrode 14 will be amplified in preamplifier 30 which will modulate a voltage controlled oscillator 26 delivering a bit rate to the clock input of counter 28. The counter 28 will be enabled for a preset time period after the sense amplifier has detected the intracardiac waveform. The count within the counter 28 at the end of the preset time will be transferred through the I/O port 20 to the microprocessor system 18. After the contents of the counter have been read it will be reset by a control signal developed by the microprocessor unit 18 and delivered to the counter 28 through the I/O port 20. Although a discrete counter is shown in FIG. 1, it should be appreciated that a counter could be implemented in software. The number transferred from the counter 28 to the microprocessor system 18 may be compared with a reference value stored in memory. If the value of the counter departs significantly from a characteristic value stored in memory the beat may be considered of abnormal origin and/or nature.

The waveform diagram of FIG. 2 clarifies the operation of the invention. Waveform A is on intracardiac electrocardiogram from a patient indicating the R-wave complexes 1–5 associated with a cardiac depolarization. Waveform complex 4 shown in Waveform A is a premature ventricular contraction (PVC) which is typically characterized by large amplitude and relatively slow slew rate excursions about the base line. Waveform B is the output of sense amplifier 24 in response to the intercardiac electrocardiogram of Waveform A. Note that shortly after the onset of the R-wave, the sense amplifier produces a logic 1 output level. This state transition initiates the operation of the one-shot 32 which enables the counter for the time-out period associated with the one-shot function.

The area under the sense amplifier output pulses in the voltage versus time plot of FIG. 2 may be a predefined function of the sense amplifier filtering that is employed. Such filtering can be adjusted for preferential sensing of different sensed signals, and multiplexed or switched filters could be advantageously utilized for this purpose.

The preamplifier 30 monitors the cardiac waveform available at terminal 14 and generates an output voltage proportional to the instantaneous value of the cardiac waveform. This voltage is supplied to the voltage controlled oscillator which produces a bit-rate dependent upon the value of the output voltage of the preamplifier. This system converts the instantaneous amplitude of the intracardiac electrocardiogram to a frequency rate supplied to counter 28. The output of the VCO is shown as Waveform D in FIG. 2.

In the FIG. 3 the value of the counter is displayed with respect to time. The counter value is zero at the start of the counting sequence. The counting sequence is initiated by the depolarization of cardiac tissue and the counts accumulate on the counter for the preset time interval. At the end of the time interval the value of the counter is read. Note that the premature ventricular contraction (PVC) results in a count higher than those for the normally conducted sinus beats.

Figure 4:
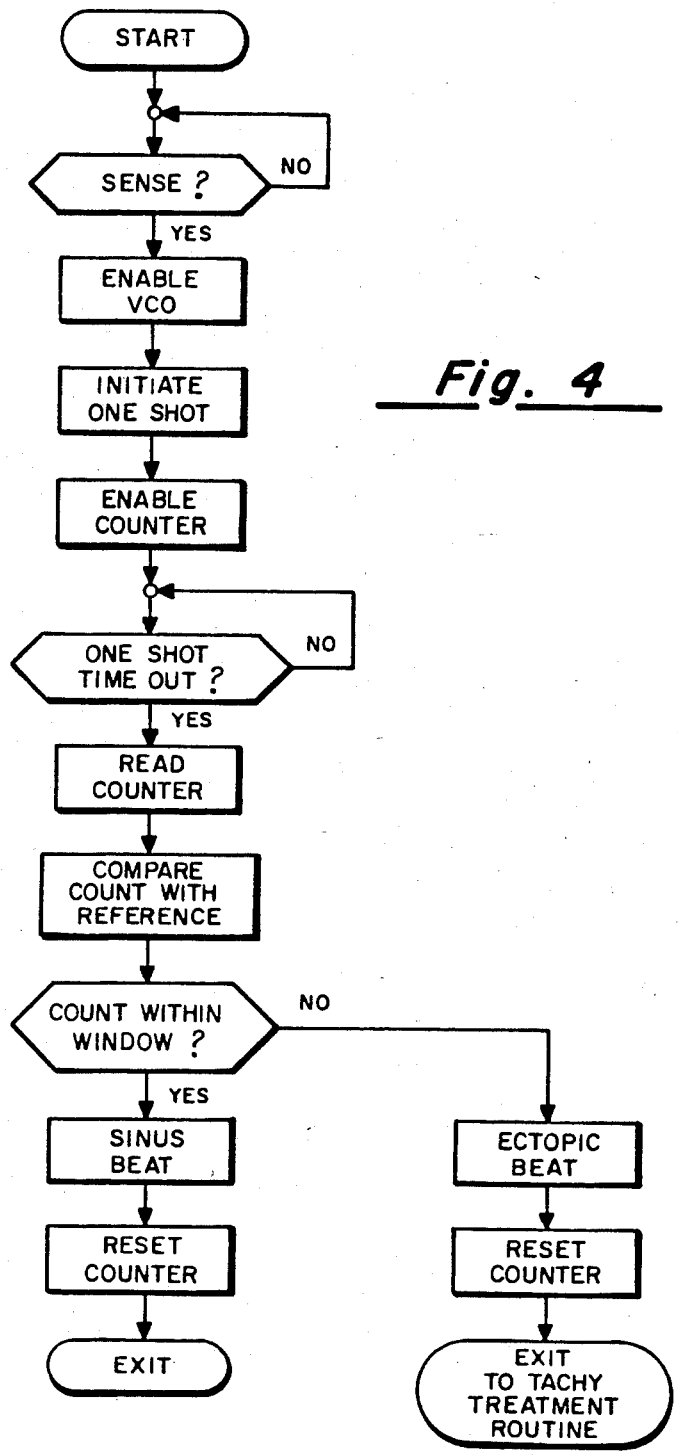

The count associated with exemplar PVC shown by complex 4 deviates from the representative count associated with the normal complexes 1, 2, 3 and 5 of Waveform A. This deviation is calculated by the microprocessor system 18. It is anticipated that a representative count number or reference value will be stored in memory and this value will be compared with the count associated with a candidate waveform. If the count of the candidate waveform is substantially higher or lower than the reference value, the beat will be classified as a non-sinus beat. The difference between the reference count and the candidate count may be non-invasively programmed to set a count window criteria shown on FIG. 4. Alternatively, the count window and reference value may be developed by the system based on a run of sinus beats.

For example, the count associated with a sequence of normally conducted sinus beats may be averaged to determine the index count. The upper and lower bounds of the count window may be taken as the highest count associated with a normally conducted complex, while the lower bound may be taken as the lowest count associated with a normally conducted beat.

The selection of the reference count and count window may be performed after the pacer is implanted. If a number of non-sinus or abnormal beats are detected within a preset time window a tachyarrhythmia treatment stimulation regime may be entered by the pacer. The occurrence of abnormal beats may be stored at specified memory locations and the value stored may be accessed by the attending physician through the telemetry system.

Although a specific embodiment of the invention has been described, it will be apparent to those skilled in the art that the scope of the present invention is intended to extend to dual chamber and atrial only applications as well as ventricular applications and for both pacing as well as tachycardia control and defibrillation systems.

What is claimed is:

1. Apparatus for comparing intracardiac depolarization waveforms comprising:
    means adapted to be coupled to the ventricle of a patient's heart for generating a logic level ventricular sense signal in response to a ventricular depolarization;
    means responsive to said sense signal for defining a count window signal;
    means for counting a clock signal, responsively enabled by said count window signal, for generating a count index;
    means for generating said clock signal, said clock signal having a frequency proportional to the instantaneous value of said ventricular depolarization;
    means for defining and storing a reference index; and
    means coupled to said means for counting for comparing the value of said count index with said reference index, to discriminate between depolarization waveforms.

2. The combination of claim 1 wherein said means for generating said clock signal having a frequency proportional to the instantaneous value of said ventricular depolarization comprises:
    preamp means adapted to be coupled to the ventricle of a patient's heart for amplifying said depolarization waveform producing an amplified signal;
    voltage controlled oscillator means responsive to said amplified signal, for generating a clock signal having a frequency substantially linearly proportional to the voltage amplitude of the ventricular depolarization.

3. The combination of claim 1 or claim 2 wherein said means responsive to said sense signal defining a count window signal comprises a monostable one-shot oscillator triggered by said sense signal for supplying an enable signal of a predetermined duration to said means for counting a clock signal.

4. A method for characterizing intracardiac waveforms comprising the sequential steps of:
    (1) controlling a voltage controlled oscillator in response to the detection of a cardiac depolarization;
    (2) initiating a one-shot multivibrator for defining a count window by periodically enabling a counter;
    (3) counting the output of the voltage controlled oscillator in the counter during the count window;
    (4) reading the contents of the counter at the conclusion of the count window;
    (5) comparing the value of the count with a reference value;
    (6) characterizing the waveform as a sinus beat if the count is within a predetermined range of the reference value and categorizing the depolarization as ectopic if the count value exceeds the predetermined range of the reference count.

* * * * *